(12) United States Patent
Biber

(10) Patent No.: US 11,774,528 B2
(45) Date of Patent: Oct. 3, 2023

(54) MAGNETIC RESONANCE TOMOGRAPHY SCANNER AND METHOD FOR TESTING

(71) Applicant: Siemens Healthcare GmbH, Erlangen (DE)

(72) Inventor: Stephan Biber, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 220 days.

(21) Appl. No.: 17/081,969

(22) Filed: Oct. 27, 2020

(65) Prior Publication Data

US 2021/0137405 A1    May 13, 2021

(30) Foreign Application Priority Data

Nov. 7, 2019   (EP) .................................. 19207566

(51) Int. Cl.
*A61B 5/055*    (2006.01)
*G01R 33/34*    (2006.01)
*G01R 33/36*    (2006.01)

(52) U.S. Cl.
CPC ........ *A61B 5/055* (2013.01); *G01R 33/34038* (2013.01); *G01R 33/3607* (2013.01); *G01R 33/3621* (2013.01); *G01R 33/3692* (2013.01)

(58) Field of Classification Search
CPC .............. A61B 5/055; G01R 33/34038; G01R 33/3607; G01R 33/3621; G01R 33/3692
See application file for complete search history.

(56) References Cited

U.S. PATENT DOCUMENTS

| | | | |
|---|---|---|---|
| 5,172,059 A | 12/1992 | Den | |
| 2004/0150401 A1* | 8/2004 | Eberler | G01R 33/583 |
| | | | 324/318 |
| 2006/0244452 A1 | 11/2006 | Den | |
| 2009/0099627 A1* | 4/2009 | Molnar | A61B 5/4082 |
| | | | 604/66 |
| 2009/0302845 A1 | 12/2009 | Biber | |
| 2011/0264165 A1* | 10/2011 | Molnar | A61N 1/36185 |
| | | | 607/45 |
| 2013/0177227 A1* | 7/2013 | Lim | G06T 11/003 |
| | | | 356/497 |

(Continued)

FOREIGN PATENT DOCUMENTS

| | | |
|---|---|---|
| DE | 68918048 T2 | 10/1994 |
| DE | 102008026849 A1 | 12/2009 |

(Continued)

OTHER PUBLICATIONS

Perrott, Prof. "High speed communication circuits and systems." (2006).pp. 1-37.

(Continued)

*Primary Examiner* — Dixomara Vargas
(74) *Attorney, Agent, or Firm* — Lempia Summerfield Katz LLC

(57) ABSTRACT

A magnetic resonance tomography scanner and a method for testing the magnetic resonance tomography scanner are provided. The magnetic resonance tomography scanner has a transmitter that is configured to transmit two-tone signals at different levels and to acquire intermodulation products of the two-tone signal with the receiver. A status of a receive path is inferred via a behavior of odd-order intermodulation products.

17 Claims, 5 Drawing Sheets

(56) References Cited

U.S. PATENT DOCUMENTS

| | | | |
|---|---|---|---|
| 2014/0225607 A1* | 8/2014 | Edwards | G01V 3/32 |
| | | | 324/303 |
| 2015/0066413 A1* | 3/2015 | Bhagat | G01R 33/56509 |
| | | | 702/104 |
| 2015/0185307 A1 | 7/2015 | He | |
| 2015/0362571 A1* | 12/2015 | Le Fur | G01R 33/465 |
| | | | 324/309 |
| 2015/0369889 A1* | 12/2015 | Grodzki | G01R 33/3856 |
| | | | 324/309 |
| 2017/0052238 A1* | 2/2017 | Le Fur | G01R 33/4625 |
| 2017/0176555 A1* | 6/2017 | Kawajiri | G01R 33/3875 |
| 2018/0275224 A1* | 9/2018 | Manickam | G01R 33/032 |
| 2018/0299522 A1* | 10/2018 | Biber | G01R 33/3415 |
| 2019/0339344 A1* | 11/2019 | Miosga | G01R 33/365 |
| 2020/0158806 A1* | 5/2020 | Okamoto | G01R 33/5673 |
| 2020/0166597 A1* | 5/2020 | Speier | H04B 13/005 |
| 2021/0121131 A1* | 4/2021 | Biber | A61B 5/721 |
| 2022/0099779 A1* | 3/2022 | Zeller | G01R 33/5608 |
| 2022/0179017 A1* | 6/2022 | Lee | G01R 33/26 |

FOREIGN PATENT DOCUMENTS

| | | |
|---|---|---|
| DE | 102015211023 A1 | 8/2016 |
| EP | 1664820 A1 | 6/2006 |

OTHER PUBLICATIONS

Rhode & Schwarz "Measuring with Modern Spectrum Analyzers—Educational Note" Feb. 2013. pp. 1-27.

Anritsu "Application Note, IMD Measurements Using Dual Source and Multiple Source Control—MS4640B Series Vector Network Analyzer" May 27, 2015 // URL: https://dl.cdn-anritsu.com/en-us/testmeasurement/files/Application-Notes/Application-Note/11410-00816C.pdf [retrieved on Apr. 28, 2020]. pp. 1-20.

European Search Report for European Application No. 19207566.1-1010 dated May 12, 2020.

Stang, Pascal P., et al. "Medusa: a scalable MR console using USB." IEEE transactions on medical imaging 31.2 (2011): 370-379.

* cited by examiner

MAGNETIC RESONANCE TOMOGRAPHY SCANNER AND METHOD FOR TESTING

This application claims the benefit of European Patent Application No. EP 19207566.1, filed on Nov. 7, 2019, which is hereby incorporated by reference in its entirety.

BACKGROUND

The present embodiments relate to a magnetic resonance tomography scanner and a method for operating the same.

Magnetic resonance tomography scanners are imaging apparatuses that, in order to map an examination object, align nuclear spins of the examination object with a strong external magnetic field and use a magnetic alternating field to excite the nuclear spins for precession about this alignment. The precession or return of the spins from this excited state into a state with less energy in turn generates, as a response, a magnetic alternating field that is received by antennas.

With the aid of magnetic gradient fields, a spatial encoding is impressed onto the signals, which then enables the received signal to be assigned to a volume element. The received signal is then evaluated, and a three-dimensional imaging representation of the examination object is provided. In order to receive the signal, local receiving antennas (e.g., local coils) may be used. The local coils are arranged directly on the examination object in order to attain an improved signal-to-noise ratio. The receiving antennas may also be installed in a patient couch.

Due to the very weak magnetic resonance signals, the image quality depends upon a proper functioning of a receive path from the antenna to the digitization and evaluation in a sensitive manner. Even minor deteriorations, as may occur in a creeping manner due to increased contact resistance at plug connections or due to degradation of structural elements, lead to a reduced image quality and increased time spent during the image acquisition.

SUMMARY AND DESCRIPTION

The scope of the present invention is defined solely by the appended claims and is not affected to any degree by the statements within this summary.

The present embodiments may obviate one or more of the drawbacks or limitations in the related art. For example, such degradations may be more easily identified.

The magnetic resonance tomography scanner according to an embodiment has a receiver and a transmitter. The transmitter is configured to generate and output a first two-tone signal with a first frequency f1 and a second frequency f2, where the first frequency f1 is not equal to the second frequency f2.

In this context, the frequency spacing is at least large enough that the signal components at f1 and f2 may be separated by the receiver (e.g., there is a relative amplitude minimum between the amplitude at f1 and the amplitude at f2). The frequency spacing may be greater than 100 Hz, 1 kHz, 10 kHz, or 100 kHz, for example. The first frequency f1, the second frequency f2, and a 3rd-order or higher-order intermodulation product (IM3) of the first frequency f1 and the second frequency f2 lie in a common receiving range of the receiver (e.g., at a Larmor frequency of the magnetic resonance tomography scanner), which is predefined by a static magnetic field strength B0 and the magnetic moment of the nuclear spins to be examined. In this context, for example, odd-order intermodulation products (e.g., 3rd-order or 5th-order or generally (2n+1)th-order intermodulation products, where n is a natural number greater than or equal to 1) may in each case have a frequency that is close to the origin frequencies f1 and f2, but with an amplitude that decreases rapidly with the order. The receiving range may be, for example, up to 1 kHz, 10 kHz, 100 kHz, 1 MHz, or 5 MHz wide, where the width is defined by an attenuation greater than 6 dB, 12 dB, or more outside the range. In this context, the receive signal may be converted into the frequency by way of mixing or digital signal processing. "Lying in a receiving range of the receiver" is also considered according to the present embodiments to be when signals with original frequencies f1, f2 and the frequency of the intermodulation product after frequency conversion may be received and evaluated by the receiver.

In this context, a level of the output two-tone signal lies in a level range in which the received two-tone signal at the receiver, as an upper limit, always continues to lie in the linear range of the receiver. The linear range may be considered to be the range with a maximum compression of the characteristic curve of less than 0.1 dB or 1 dB. In this context, the level of an inherent noise of the receiver, or a signal spacing between the IM3 and this noise level of 3 dB, 6 dB or more, is considered the lower limit of the level range.

The outputting of the signal by the receiver in this context may be the outputting via an antenna (e.g., a body coil) or also via another electrical or magnetic antenna as an electromagnetic alternating field. For diagnosis, however, it is also conceivable for the output signal to be directly coupled in via a signal loop at different diagnosis points (e.g., galvanically, inductively or capacitively). The levels of the two-tone signals required at the injection point then in each case depend upon the amplification or attenuation on the signal path between injection point and receiver.

In this context, the transmitter may be the transmitter of the magnetic resonance tomography scanner for exciting the nuclear spins, provided that the output level thereof may be sufficiently reduced. A sufficient linearity is also necessary in the lower power range. In one embodiment, the required low signal may be generated directly from the input signal of the output stage, bypassing the output stage. In one embodiment, however, a dedicated transmitter for generating the two-tone signals may be provided, or, instead of the power output stage, a linear low signal amplifier in the transmitter may be provided.

In one embodiment, the magnetic resonance tomography scanner is configured to transmit a second two-tone signal that differs from the first two-tone signal in level.

The method according to the present embodiments is provided for functional testing of a receive chain with a magnetic resonance tomography scanner according to the present embodiments. In this context, the receive chain may include all elements in the signal path from the antenna (e.g., local coil or body coil) up to the digitization in the receiver and the downstream image reconstruction. In one embodiment, however, only parts thereof may be tested, for example, in order to localize a fault more precisely.

In one act of the method, the transmitter, controlled by a controller of the magnetic resonance tomography scanner, outputs a first two-tone signal at a first level. As already presented for magnetic resonance tomography scanners, the outputting may be an outputting via an antenna, or, for example, also a coupling via a signal loop into a diagnosis point of a receive path. In this context, the level of the first two-tone signal is predetermined such that the level lies at least above a noise level of the receiver, when the first two-tone signal has passed through the signal path up to the receiver or the analysis facility.

In a further act, the analysis facility acquires a first intermodulation product via the signal loop. In an embodiment, the analysis facility is provided in this context by components of the magnetic resonance tomography scanner (e.g., a receiver for the magnetic resonance signals for preparing the radio frequency and the subsequent signal processing of the image reconstruction for the evaluation via a Fourier transform). The signal loop may include, for example, all components of the receive path from an antenna coil up to the receiver, or also only parts from a diagnosis point on the receive path up to the receiver, in order to localize an error more precisely. In one embodiment, a radio frequency preparation and signal analysis may take place in a separate analysis facility. In one embodiment, amplitudes of the IM3 and at f1 and f2 are acquired, for example.

In a further act, the transmitter outputs a second two-tone signal at a second level. The second two-tone signal may differ from the first two-tone signal in level. For example, the second two-tone signal may have a level greater by at least 3 dB, 6 dB, 12 dB or even higher provided that the condition of the linear range, as has been defined previously, is met. The change in level, for both frequencies f1 and f2 of the two-tone signal, also takes place in the same direction, providing that a change in the odd-order (e.g., third-order intermodulation signal) is not compensated partially.

In a further act, the analysis facility acquires a second intermodulation product via the signal loop. What has already been presented regarding the acquisition of the first two-tone signal applies here.

In principle, a sequence of the first two-tone signal and the second two-tone signal is interchangeable (e.g., whether transmitting first takes place at a higher or lower level only slightly changes the subsequent ascertaining).

In a further act, a test value is ascertained as a function of the level of the first two-tone signal, the level of the second two-tone signal, a level of the first intermodulation product, and a level of the second intermodulation product. By way of two-tone signals with different levels, it is possible in this context to eliminate an influence of an attenuation that is constant over both measurements (e.g., by way of coupling-in members, such as when measuring via an antenna coil of a local coil by way of the spatial arrangement), and to ascertain a test value that is independent thereof. If the attenuation is known, however, then, in principle, an individual measurement with one two-tone signal would also be sufficient in order to ascertain a test value. A plurality of measurements may then be used in order to reduce noise, for example, or to eliminate other level-dependent parameters.

In a further act, the analysis facility compares the ascertained test value with a predetermined reference value. The predetermined test value may be ascertained by a reference measurement on commissioning, in the laboratory or also from simulations, for example. The comparison may also take place by way of the controller of the magnetic resonance tomography scanner, providing that this is part of the analysis facility.

In another act, a signal is output to an operator on an output device, or a signal is output to a controller of the magnetic resonance tomography scanner as a function of the comparison. If the signal indicates a deviation from a reference value that leads to a deterioration in the image, then the controller or the operator is able to interrupt an image acquisition. A service measure may also be prompted in order to rectify the error. In one embodiment, the controller may repeat the acts of the method with a modified signal loop.

In one embodiment, a magnetic resonance tomography scanner with a transmitter with two-tone signal and with the intermodulation product that is sensitive to modifications according to the present embodiments makes it possible to identify odd-order (e.g., third-order) deteriorations in the receive chain at an early stage. In this context, the different levels make it possible to eliminate variations in level (e.g., when coupling in) in the evaluation.

In one embodiment of the magnetic resonance receiver, the magnetic resonance tomography scanner has an analysis facility. The analysis facility is configured to determine a level of the intermodulation product in an input signal. The analysis facility may be part of the image reconstruction, for example. A dedicated signal processor or a signal processing component of the receiver may also be provided, however. The level of the intermodulation product may take place, for example, by way of an analog or digital filter and subsequent amplitude measurement, or directly by a Fourier transform of the digitized signal.

By way of the intermodulation product, a particularly sensitive identification of deviations in the receive chain is possible.

In one embodiment of the magnetic resonance tomography scanner, the magnetic resonance tomography scanner has a signal loop. The signal loop is configured to couple the two-tone signal of the transmitter into a component of a receive path of the receiver. In this context, a signal loop may be any signal connection that conducts a two-tone signal, which is output by the transmitter, via one or more components of a receive path of the magnetic resonance tomography scanner to the receiver (e.g., the receiver for magnetic resonance signals), including the signal processing acts contained therein.

Via the signal loop, the two-tone signal may be coupled into the receive path of the magnetic resonance tomography scanner as a test signal.

In one embodiment, the magnetic resonance tomography scanner according to the present embodiments has a local coil. The signal loop includes the local coil (e.g., the two-tone signal is coupled into the local coil and passes through the receive path up to the receiver). In one embodiment, the signal loop includes an antenna coil of the local coil in this context (e.g., the two-tone signal is coupled into the antenna coil in an inductive manner). In one embodiment, however, the local coil may have a diagnosis terminal for connecting to the signal loop, so that a diagnosis signal may be electrically coupled in directly. In one embodiment, the two-tone signal may also be coupled in optically and converted into an electrical signal by a photoelectric converter.

In one embodiment, the magnetic resonance tomography scanner also makes it possible to test the functioning of the local coil.

In one possible embodiment, the magnetic resonance tomography scanner has a signal splitter in the signal path. The signal splitter may be embodied by one or more electronic or mechanical switches, for example, which may also be interconnected in a matrix. The signal splitter has at least one signal input for the two-tone signal and at least two signal outputs, which may be connected to the signal input by way of the controller. A controller of the magnetic resonance tomography scanner is configured to couple the two-tone signal of the transmitter into different components of the receive path using the signal splitter. For example, the signal outputs of the signal splitter may be connected directly to the local coil and a terminal of the local coil on the receiver. By feeding the two-tone signal once into the local coil and once directly into the receiver, the signal splitter makes it possible to localize an error in the local coil.

In one embodiment, the signal splitter makes it possible to localize errors on individual sections of the receive path.

In one embodiment of the method, the act of ascertaining a test value includes the determining of an output intermodulation intercept point 3 (OIP3). In this context, the OIP3 is a virtual point in a dual logarithmic amplifier characteristic curve, in which the 3rd-order intermodulation product of two signals would be a two-tone signal in the amplitude equal to the fundamental signals of the two-tone signal. The OIP3 may be interpolated from the values for acquired amplitudes of two two-tone signals of different levels and the amplitudes of the 3rd-order intermodulation product generated therefrom.

In one embodiment, the OIP3 is independent of the precise coupling strength of the transmitter into the receive loop and is simultaneously sensitive to modifications in the receive path, providing that modifications and errors may be readily identified.

In one possible embodiment of the method, the magnetic resonance tomography scanner according to the present embodiments has a signal splitter, where the act of adjusting the signal splitter by way of the controller takes place before the act of outputting a two-tone signal. By adjusting the signal splitter, an output of the signal splitter is coupled to a component of the receive path; thus, a signal loop is established from the transmitter, via the signal splitter, to the receiver, providing that a two-tone signal may reach the receiver, where the two-tone signal may be evaluated.

In one embodiment, by way of the signal splitter, the signal loop may be closed via different components, and thus, a possible error may be narrowed down by repeating the method with different signal loops.

The above-described characteristics, features, and advantages of the present embodiments, as well as the manner in which these are achieved, will become clearer and more readily understandable in connection with the following description of the exemplary embodiments, which are explained in more detail in conjunction with the drawings.

DETAILED DESCRIPTION

Figure 1:
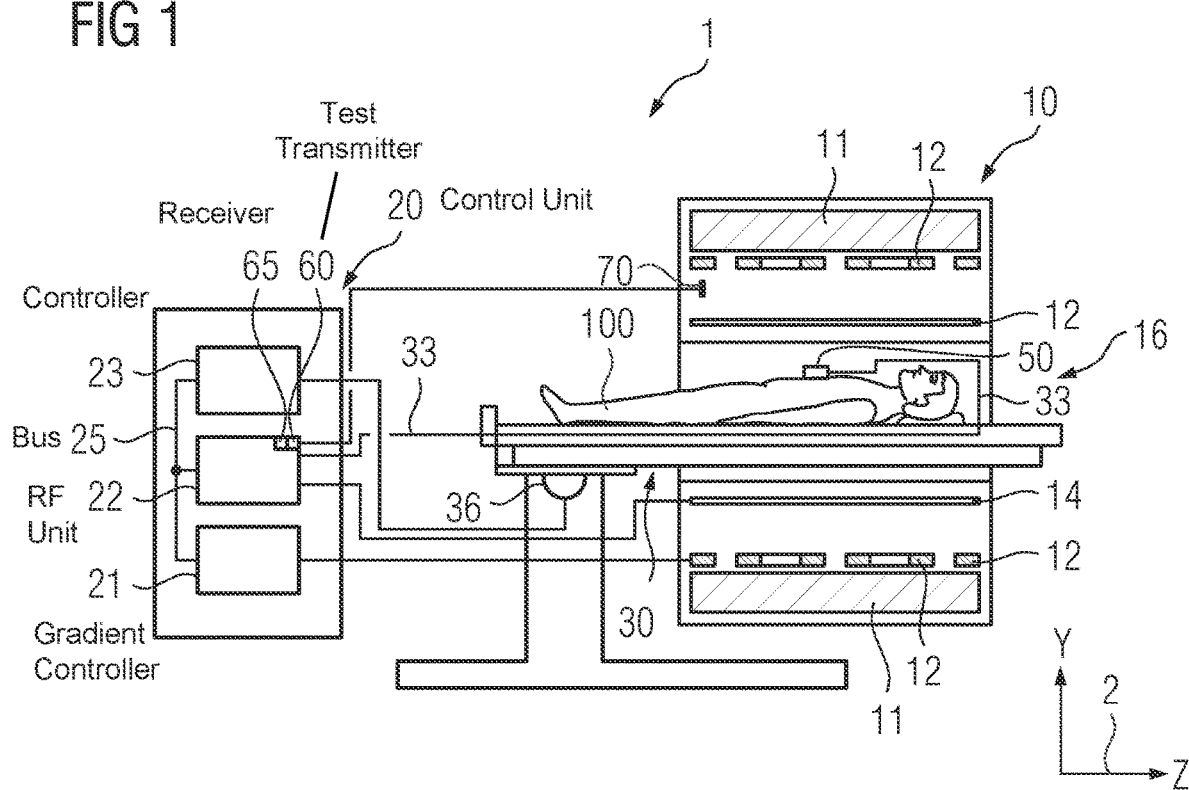
FIG. 1 shows a schematic representation of a magnetic resonance tomography scanner according to an embodiment.

FIG. 1 shows a schematic representation of an embodiment of a magnetic resonance tomography scanner 1.

The magnet unit 10 has a field magnet 11 that generates a static magnetic field BO for aligning nuclear spins of samples or of the patient 100 in a recording region. The recording region is characterized by an extremely homogeneous static magnetic field BO, where the homogeneity relates, for example, to the magnetic field strength or the absolute value. The recording region is virtually spherical in shape and is arranged in a patient tunnel 16 that extends in a longitudinal direction 2 through the magnet unit 10. A patient couch 30 may be moved in the patient tunnel 16 by the positioning unit 36. Usually, the field magnet 11 involves a superconducting magnet that is able to provide magnetic fields having a magnetic flux density of up to 3 T, or even more in more recent devices. For lower field strengths, however, permanent magnets or electromagnets having normally conducting coils may also be used.

In addition, the magnet unit 10 has gradient coils 12 that are configured to overlay the magnetic field BO with variable magnetic fields in three spatial directions for the purpose of spatially differentiating the acquired mapping regions in the examination volume. The gradient coils 12 are usually coils made from normally conductive wires that may generate fields orthogonal to one another in the examination volume.

The magnet unit 10 also has a body coil 14 that is configured to radiate a radio frequency signal supplied via a signal line into the examination volume and is configured to receive resonance signals emitted by the patient 100 and output the resonance signals via a signal line.

A control unit 20 (e.g., a controller) supplies the magnet unit 10 with the various signals for the gradient coils 12 and the body coil 14 and evaluates the received signals.

Accordingly, the control unit 20 has a gradient controller 21 that is configured to supply the gradient coils 12 via supply lines with variable currents that provide the desired gradient fields in the examination volume in a time-coordinated manner.

In addition, the control unit 20 has a radio frequency unit 22 that is configured to generate a radio frequency pulse having a predefined temporal sequence, amplitude, and spectral power distribution for exciting a magnetic resonance of the nuclear spins in the patient 100. Pulse powers in the kilowatt range may be achieved in this case. The excitation pulses may be radiated into the patient 100 via the body coil 14 or also via a local transmit antenna.

A controller 23 communicates with the gradient controller 21 and the radio frequency unit 22 via a signal bus 25.

A local coil 50 is arranged on the patient 100 and is connected to the radio frequency unit 22 and receiver 65 of the radio frequency unit 22 via a connecting line 33.

Due to the weak magnetic resonance signals, the results of a magnetic resonance tomography strongly depend upon the receive quality (e.g., upon the signal-to-noise ratio (SNR)). In this context, the SNR may be deteriorated in a creeping manner due to the degradation of structural elements, without immediate failures occurring. The image quality or the required measurement duration may, however, change as a result. It is therefore advantageous if the components involved in receiving have sensitivity tested, at least before each image acquisition, in the configuration provided for the image acquisition with the magnetic resonance tomography scanner.

It is difficult to measure the receive properties with the involvement of all components, as due to environmental parameters, such as the geometric arrangement of the movable local coils 50 and variable attenuation by the patient 100, for example, the properties of the receive path are mixed with these external influences.

It is therefore a key idea of the present embodiments to eliminate these additional variables via a plurality of measurements.

Figure 2:
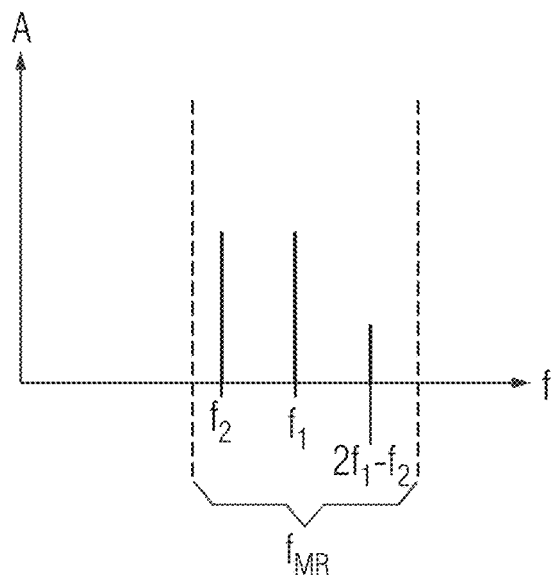
FIG. 2 shows a schematic representation of frequencies of exemplary signals that are used in a method according to an embodiment.

In FIG. 2, frequencies of signals used, by way of example, are shown in this context. In the diagram, the amplitudes A of the signals in any given units are plotted against the frequency f of the signals. All signals used fall, for example, in a frequency range $f_{MR}$ that also corresponds to a receiving range of the receiver 65. This receiving range is usually arranged around the Larmor frequency, which is defined by the static magnetic field BO and the nuclear spins to be examined. A typical bandwidth is less than 100 kHz, 500 kHz, or 1 MHz.

This may be achieved, for example, by two frequencies f1 and f2 that lie close to one another being selected in the frequency range $f_{MR}$. An odd-order intermodulation product may then lie close to the two generating frequencies f1 and f2. For example, a frequency of the 3rd-order intermodulation product (IM3), according to the formula $f_{IM3}=2f_1-f_2$, as shown, lies adjacent to the frequencies $f_1$ and $f_2$, displaced upward by the frequency difference. In one embodiment, in this context, the signal generated by the test transmitter 60 itself has no or only a negligible component of an IM3 signal (e.g., with an attenuation of 20 dB, 40 dB, 60 dB or more). In the receiver, the IM3 signal may then be assigned to the receive path and may be evaluated more easily, as the IM3 signal is not a change, but rather, is substantially the absolute value that may be considered in the analysis.

Figure 3:
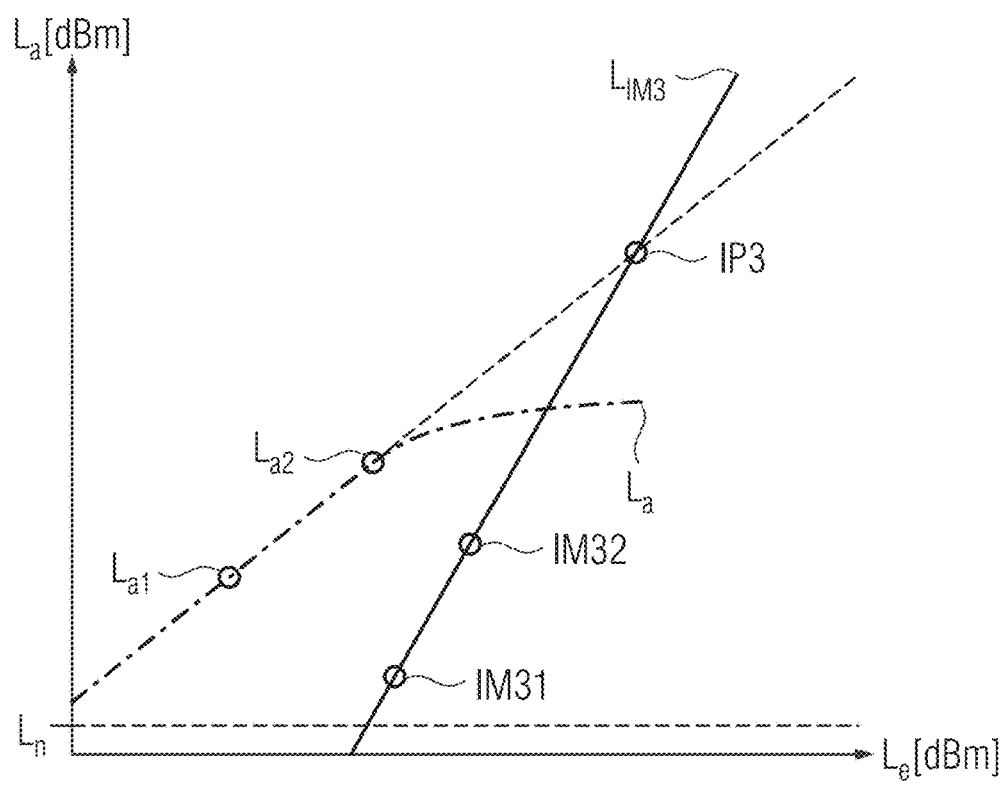
FIG. 3 shows a schematic representation of levels of the signals used in the method, as well as a possible evaluation.

FIG. 3 schematically shows a diagram of one embodiment of a method for assessing the receive chain. An input level is plotted horizontally in a logarithmic scale. This may then correspond to the level of one of the two input signals of the two-tone signal with the frequencies $f_1$ and $f_2$, or may be derived from both. In one embodiment, the levels are equal or in a fixed ratio to one another in order to simplify the evaluation. In the diagram, the input level may then be represented by a single value on the horizontal axis.

At each input level, the corresponding output levels $L_a$ are measured. In this context, the output levels of the output signals generated from the two-tone signal with $f_1$ and $f_2$ by the linear amplification and the higher-order intermodulation product (e.g., IM3) generated by non-linear amplification may be separated based on the frequency by filters or a Fourier transform, and the level may be determined separately for each frequency. In this manner, at least two output values, in the diagram $L_{ax}$ and $IM3_x$, which are plotted as points in the coordinate system, are obtained for each input signal $L_e$. In one embodiment, the input level $L_e$ is chosen such that, for example, the output levels La and IM3 lie above a noise level $L_n$ of the receive loop. For two different input levels, a total of four points are obtained in this manner.

Since the amplification in the receive loop is linear in a first approximation, a characteristic curve of the amplification of the overall receive loop is therefore defined by the points $L_{a1}$ and $L_{a2}$ and a straight line through these points. Due to compression at the upper end of the linear range, this bends into a horizontal line, in which the output level is independent of the input signal level due to saturation. In this context, the input levels $L_e$ may be chosen such that the output levels lie below this bend in the linear range of the receive loop. In one embodiment, a large number of input levels $L_e$ may be used, and associated output levels $L_a$ and IM3 may be measured. From these, only the value pairs that lie in the linear range and above the noise level may be chosen.

The intermodulation products also increase together with the input level, but as a result of the higher order, also with a higher exponent, steeper by a factor of 3 in the IM3. A straight line is also specified by two points $IM3_1$ and $IM3_2$ here. As a result of the different inclines, the straight lines for the linear components La and the IM3 intersect at a point that is designated 3rd-order intercept point (e.g., intercept point 3, IP3). Even if this point cannot be measured in real terms due to the compression being applied, it is nevertheless characteristic for the amplification properties of the receive loop. For example, it is insensitive to parallel displacement in the abscissa, as is caused, for example, by different coupling-in attenuation of the two-tone signal due to modifying the position of a local coil 50, because both straight lines are displaced by the same value in the abscissa, providing that this change is offset again when determining the intercept point.

The principle of the present embodiments is not restricted to the IP3. For example, higher, odd-order intercept points such as IP5 or IP7 may also be used. A large number of mathematically equivalent calculations may also be provided in the context of the method according to the present embodiments, which eliminate variable factors of the method, such as the coupling strength, by using a plurality of measurement points for linear output signal and intermodulation product. In this context, the embodiment shown in FIG. 3 has been chosen, for example, due to clearness in the diagram.

Figure 4:
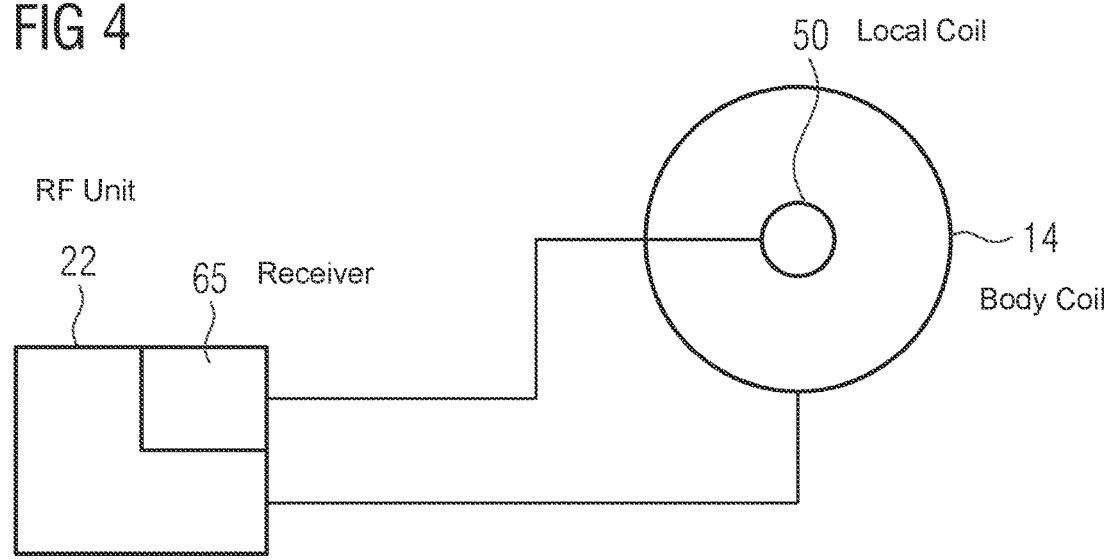
FIG. 4 shows a schematic representation of facilities of a magnetic resonance tomography scanner involved in a method, according to an embodiment.

FIG. 4 shows an embodiment of the components that have been used for the method according to the present embodiments, of a magnetic resonance tomography scanner 1 according to the present embodiments. The radio frequency unit 22 generates the two-tone signal with, for example, the frequencies $f_1$ and $f_2$ and transmits these via the body coil 14. In principle, the radio frequency unit 22 is configured to generate signals with a frequency around the Larmor frequency in order to excite the nuclear spins. In this context, it is necessary for the radio frequency unit 22 to be configured to also generate signals with sufficiently low amplitude and enough linearity, so that these do not override the receiver 65 or lead to compression and, at the same time, an IM3 signal with considerable amplitude is not itself already generated. Details regarding the transmit section or the test transmitter 60 are explained in further detail with reference to FIG. 6.

The two-tone signal is inductively coupled into the receive coil via the local coil 50 or the antenna coil thereof. In this manner, all components of the receive path involved in the receiving may be tested via the antenna coil and LNB of the local coil 50, signal connections, plug connectors, switching matrix, up to the receiver 65. For example, the controller 23 of the magnetic resonance tomography scanner 1 is able to control the generation of the two-tone signal via the radio frequency unit 22 and the evaluation of the signal received by the receiver 65 according to the method according to the present embodiments.

Figure 5:
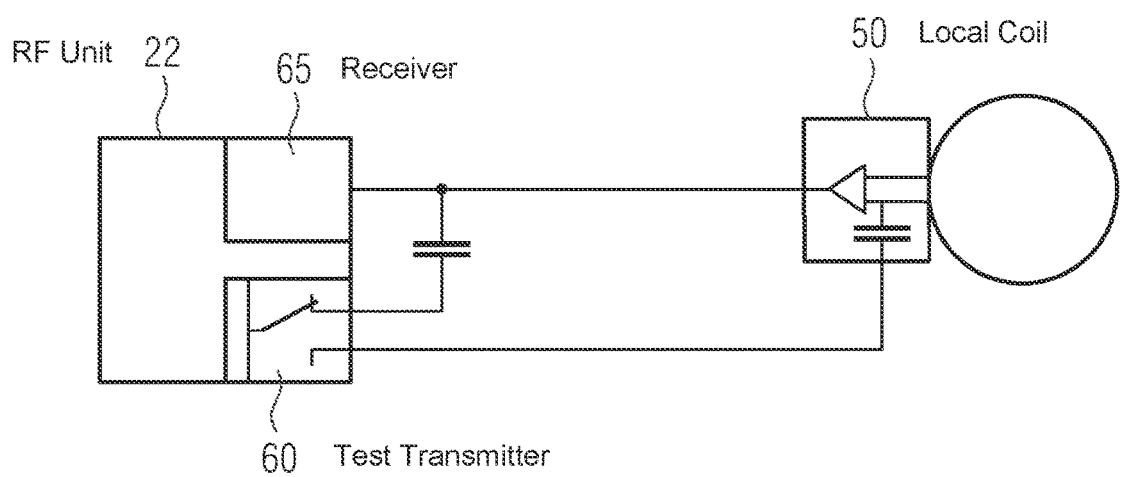
FIG. 5 shows a schematic representation of facilities involved in the method according to one embodiment of the magnetic resonance tomography scanner.

In FIG. 5, another embodiment of the magnetic resonance tomography scanner according to the present embodiments is shown by way of example. In this context, the test transmitter 60 has a switch or a switching matrix, with which the two-tone signal optionally may be coupled into the receive loop at different points. Two injection points with capacitive coupling are indicated here by way of example. One injection point is at the input of the LNB in the local coil 50; the other injection point is at the input to the receiver 65. In this manner, it is possible to carry out the method according to the present embodiments for both injection points in succession, and thus to localize or exclude a possible problem in the local coil 50. By coupling in directly, different coupling due to geometric factors may also be excluded.

In this context, the test transmitter 60 may be the same transmitter that is also used to excite the nuclear spins, only parts thereof such as a transmit signal preparation without power output stage, or even a dedicated test transmitter with independent signal generation. A separate test transmitter 60 may be optimized with regard to linearity in a particularly simple manner.

Figure 6:
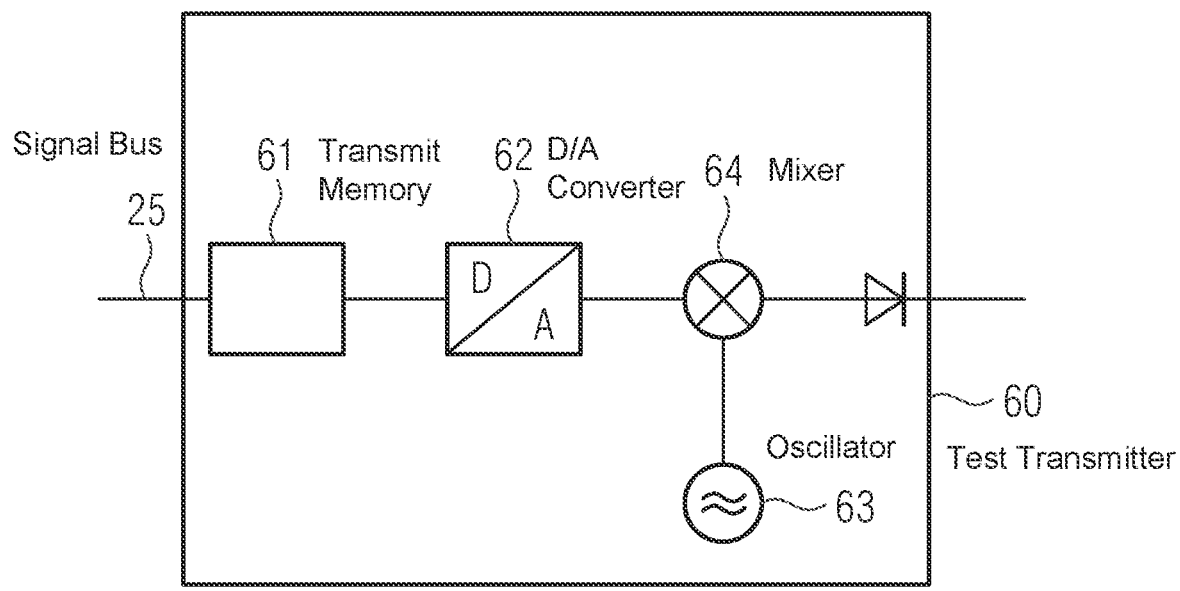
FIG. 6 shows a schematic representation of a transmitter used in the method according to an embodiment.

FIG. 6 schematically shows a possible embodiment of a test transmitter 60, as is conceivable both as an integrated transmitter for exciting the nuclear spins (e.g., at least in the signal preparation) or also as a dedicated test transmitter 60. In this context, the test transmitter 60 has a transmit memory 61, into which the controller 23 is able to write a transmit signal via the signal bus 25. For example, this may be an envelope curve or explicitly a signal in a baseband in the form of a series of real or complex amplitude values. The signal is read out by a D/A converter 62 and transformed into an analog signal. By mixing with an intermediate frequency, generated by an oscillator 63, in a mixer 64, the signal is converted into the desired frequency range $f_{MR}$ around the Larmor frequency.

The digital provision of the baseband signal allows any frequency and amplitude distribution (e.g., also the generation of the baseband signal). The targeted excitation of individual layers in an MR image acquisition may also be provided. In this embodiment, the test signal essentially differs from an excitation signal for the nuclear spins due to the subsequent amplification. While signals at a few microwatts to milliwatts at higher linearity are to be provided for the method according to the present embodiments, depending on the coupling, an end stage is to provide hundreds of watts to kilowatts of power for excitation. The test transmitter 60 is therefore also able to be provided by a part of a transmitter for exciting nuclear spins, without or with specific low-power output stage.

In principle, however, a simple combination of two oscillators, a summator, and an adjustable amplification may also be provided as a pure test transmitter.

Figure 7:
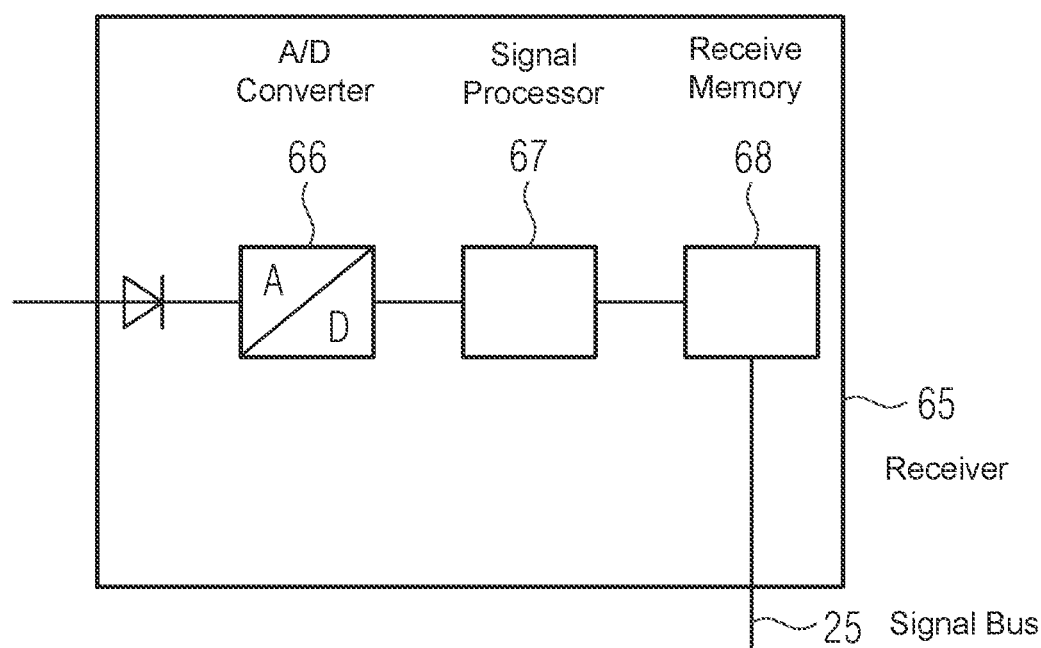
FIG. 7 shows a schematic representation of a receiver used in the method according to an embodiment.

FIG. 7 shows a receiver 65, as is also used for receiving the MR signals. The incoming analog signal is amplified and, if necessary, filtered. It is also possible to convert to an intermediate frequency or baseband that may take place in the receiver or also in a preceding stage such as the local coil 50. The analog signal is digitized by an A/D converter 66, digitally processed further by a signal processor 67 or an FPGA, and provided in a digitized form in a receive memory 68 of the controller 23, which is able to access this via the signal bus 25. The separation of the frequencies $f_1$, $f_2$ and the IM3, as well as the assessment of the level, may take place already in the signal processor 67 in this context, for example, or may first take place by way of the controller 23.

During the evaluation, a possible analog or digital frequency conversion is also taken into consideration, by way of which the frequencies $f_1$, $f_2$ and that of the IM3 are converted into the baseband.

Figure 8:
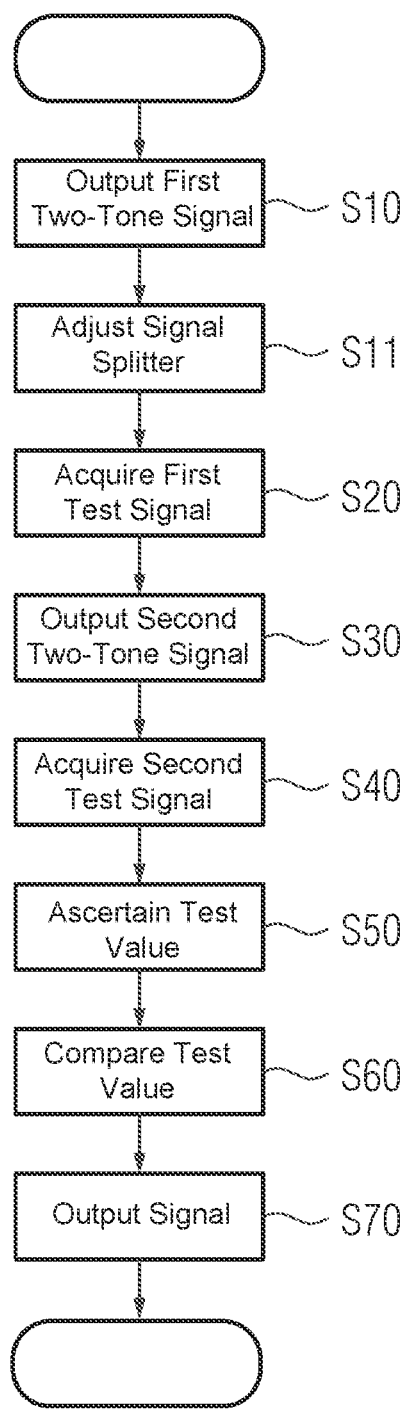
FIG. 8 shows a schematic flow diagram for an exemplary method according to an embodiment.

FIG. 8 schematically shows a flow diagram of an embodiment of the method.

In act S10, the test transmitter outputs a first two-tone signal. The properties of the test transmitter and of the two-tone signal have already been explained in detail with reference to the preceding figures. The transmission may take place via an antenna, or also directly via an electrical signal connection into the receive path. The test signal is conducted for acquisition via the signal loop provided in this way, from the test transmitter 60 up to the analysis facility (e.g., the receiver 65).

It is also conceivable that, in this context, in act S11, the signal splitter (e.g., a switching matrix) is adjusted in order to inject the test signal at a predetermined point via the switching matrix and thus to close the signal loop. By repeating the method with various settings of the signal splitter and injection points associated therewith, an error in the receive path may thus be localized more precisely.

In a further act, the analysis facility acquires a first test signal with a first intermodulation product via the signal loop. "Acquire" may be, for example, at least that an amplitude of the two-tone signal (e.g., of one or both tone signals) and of the intermodulation signal are ascertained in the received test signal. Acquire may also, however, include the digitization of the first test signal and optionally storage, providing that the subsequent evaluation takes place with digital signal processing procedures, such as filtering or FFT, for example.

In a further act S30, the test transmitter outputs a second two-tone signal at a second level by way of the transmitter. In this context, the first two-tone signal differs from the first two-tone signal at least in level. In one embodiment, the frequencies and the amplitude ratio remain unchanged, but it is also conceivable to modify these in a predetermined manner that may therefore be accounted for in the evaluation.

In a further act S40, the analysis facility acquires a second test signal with the second two-tone signal and a second intermodulation product via the signal loop. The statements made with reference to act S20 apply here.

In act S50, the analysis facility ascertains a test value as a function of the level of the first two-tone signal, the level of the second two-tone signal, a level of the first intermodulation product, and a level of the second intermodulation product. The test value may be the output intercept point 3 OIP3 shown in relation to FIG. 3, but may also be other test values that may be obtained mathematically through equivalent remodelings, or test values in which a variable coupling between test transmitter 60 and analysis facility is eliminated.

In act S60, the analysis facility compares the test values with a reference value. For example, the analysis facility is able to establish whether the test value lies below or above a limit value or within or outside a window or value range.

In a further act S70, the analysis facility outputs a signal to a controller 23 of the magnetic resonance tomography scanner 1 or a display for an operator, as a function of the result of the comparison. For example, a notification that states that the receive path is degraded may if the value for the OIP3 has fallen below a threshold value.

Although the invention has been illustrated and described in greater detail with the exemplary embodiments, the invention is not restricted by the examples disclosed, and other variations may be derived therefrom by the person skilled in the art without departing from the protective scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A magnetic resonance tomography scanner comprising:
   a receiver;
   a transmitter, wherein the transmitter is configured to generate and output a first two-tone signal with a first frequency, a second frequency, and a level; and
   a coil configured to receive the first two-tone signal directly from the transmitter,
   wherein the first frequency, the second frequency, and an odd-order or higher-order intermodulation product of the first frequency and the second frequency lie in a receiving range of the receiver,
   wherein the first frequency is not equal to the second frequency, and
   wherein the level of the output first two-tone signal lies in a level range in which the received two-tone signal at the receiver lies in a linear range of the receiver, and the odd-order intermodulation product lies above a noise level of the receiver.

2. The magnetic resonance tomography scanner of claim 1, wherein the transmitter is configured to transmit a second two-tone signal that differs from the first two-tone signal in level.

3. The magnetic resonance tomography scanner of claim 1, further comprising an analysis facility that is configured to determine a level of the intermodulation product in an input signal of the receiver.

4. The magnetic resonance tomography scanner of claim 1, further comprising a signal loop that is configured to couple the first two-tone signal of the transmitter into a component of a receive path of the receiver.

5. The magnetic resonance tomography scanner of claim 4, wherein the coil is a local coil, and
   wherein the signal loop comprises the local coil.

6. The magnetic resonance tomography scanner of claim 4, further comprising:
   a signal splitter in a signal path; and
   a controller configured to couple the first two-tone signal of the transmitter into different components of the receive path using the signal splitter.

7. The magnetic resonance tomography scanner of claim 2, further comprising an analysis facility that is configured to determine a level of the intermodulation product in an input signal of the receiver.

8. The magnetic resonance tomography scanner of claim 2, further comprising a signal loop that is configured to couple the first two-tone signal of the transmitter into a component of a receive path of the receiver.

9. The magnetic resonance tomography scanner of claim 8, wherein the coil is a local coil, and
   wherein the signal loop comprises the local coil.

10. The magnetic resonance tomography scanner of claim 8, further comprising:
    a signal splitter in a signal path; and
    a controller configured to couple the first two-tone signal of the transmitter into different components of the receive path using the signal splitter.

11. The magnetic resonance tomography scanner of claim 7, further comprising a signal loop that is configured to couple the first two-tone signal of the transmitter into a component of a receive path of the receiver.

12. The magnetic resonance tomography scanner of claim 11,
    wherein the coil is a local coil, and wherein the signal loop comprises the local coil.

13. The magnetic resonance tomography scanner of claim 11, further comprising:
    a signal splitter in a signal path; and
    a controller configured to couple the first two-tone signal of the transmitter into different components of the receive path using the signal splitter.

14. A method for functional testing of a receive chain with a magnetic resonance tomography scanner, the method comprising:
    outputting, by a transmitter, a first two-tone signal at a first level;
    directly receiving, by a coil, the output first two-tone signal;
    acquiring, by an analysis facility, a first test signal with a first intermodulation product via a signal loop, the signal loop including the coil;
    outputting, by the transmitter, a second two-tone signal at a second level, the outputting of the second two-tone signal being after the outputting of the first two-tone signal, wherein the second two-tone signal differs from the first two-tone signal in level;
    acquiring a second test signal with a second intermodulation product via the signal loop by way of the analysis facility;
    ascertaining a test value as a function of the level of the first two-tone signal, the level of the second two-tone signal, a level of the first intermodulation product, and a level of the second intermodulation product;
    comparing, by the analysis facility, the test value with a reference value; and
    outputting a signal to a controller of the magnetic resonance tomography scanner or a display for an operator, as a function of the comparison.

15. The method of claim 14, wherein ascertaining the test value comprises determining an OIP3.

16. The method of claim 14, wherein the outputting comprises adjusting a signal splitter such that the signal loop is provided.

17. The magnetic resonance tomography scanner of claim 1, wherein the coil is a local coil or a body coil.

* * * * *